US00PP32943P3

(12) United States Plant Patent
Clark

(10) Patent No.: US PP32,943 P3
(45) Date of Patent: Mar. 30, 2021

(54) COLEUS PLANT NAMED 'UF17-64-1'

(50) Latin Name: *Plectranthus scutellarioides*
Varietal Denomination: UF17-64-1

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/873,455

(22) Filed: Apr. 16, 2020

(65) Prior Publication Data

US 2020/0367411 P1 Nov. 19, 2020

Related U.S. Application Data

(60) Provisional application No. 62/920,844, filed on May 17, 2019.

(51) Int. Cl.
*A01H 5/02* (2018.01)
*A01H 6/00* (2018.01)
*A01H 5/12* (2018.01)

(52) U.S. Cl.
USPC ..... Plt./469
CPC ..... *A01H 6/00* (2018.05); *A01H 5/12* (2013.01)

(58) Field of Classification Search
USPC ..... Plt./469
CPC ..... A01H 6/00; A01H 5/12
See application file for complete search history.

*Primary Examiner* — Keith O. Robinson
(74) *Attorney, Agent, or Firm* — Katherine Koenig; Koenig IP Works, PLLC

(57) ABSTRACT

'UF17-64-1' is a new coleus plant with a combination of novel characteristics which include vigorous compact mounded growth habit, excellent heat tolerance, and consistent crimson foliage. It has superior stability in foliage color in both sun and shade conditions, maintaining stable color in all conditions. 'UF17-64-1' has not been observed to produce flowers in any trial we have conducted to date, so it has long season performance as an annual plant in the landscape until late Fall.

3 Drawing Sheets

Genus and species: *Plectranthus scutellarioides.*

Cultivar denomination: The present disclosure relates to coleus cultivar 'UF17-64-1'.

BACKGROUND OF THE NEW CULTIVAR

Coleus (previously *Solenostemon scutellarioides,* now *Plectranthus scutellarioides*) plants are used as annual bedding plants for the landscape and mixed containers in summer gardens. Coleus plants are popular to commercial growers and landscapers because they are easy to propagate and provide fast and reliable attractive foliage color that makes their businesses profitable. Coleus plants are also popular with home gardeners because they are easy to grow in both full sun and partial shade conditions, and require less maintenance than many other annual garden plants. From the breeder perspective, there is much genotypic variability in coleus because it is a tetraploid with active transposons and there are a number of different visible phenotypes including foliage color, leaf shape and size, plant height, time to flowering and growth habit.

The coleus breeding program at the University of Florida in Gainesville, Fla. was initiated in 2003 with an emphasis on developing new clonally propagated cultivars that are profitable for producers and perform well in consumer gardens with little or no care. Using recurrent mass selection and maintaining a large pool of germplasm our program has released a number of cultivars into the industry over the past decade. The coleus breeding program has focused on screening for new cultivars with novel leaf colors and shapes, increased vigor and branching, and late flowering, by conducting greenhouse and field trials under demanding environmental conditions. Greenhouse trials under "lush" conditions that push the plants to grow as fast as possible with high amounts of light, high fertility and high temperatures are used because these conditions allow for rapid discernment of growth habits and vigor characteristics, and also facilitate observation of plant phenotypes under conditions where greenhouse pathogen and insect pressure is highest. Field trials at Citra, Fla. are planted in full sun in sand beds with plastic mulch in May each year with drip irrigation and a minimal amount of slow-release fertilizer added at planting. Field trials at Gainesville, Fla. are planted in 30% shade in sand beds in May each year with drip irrigation and a minimal amount of slow-release fertilizer added at planting. These "lean" growing conditions are used in the field trials to screen for plants that grow vigorously and consistently for minimalist gardeners. Coleus produces a better seed crop under "lean" conditions than "lush" conditions, which is useful for making open-pollinated seeds. Since data is collected on a large number of genotypes (~600-800 per year), each trial only contains 1-3 plants per genotype. If a genotype performs poorly in any trial it is automatically discarded from the program, leaving ~200-250 genotypes in the program as elite stock at the end of each year.

Desirable characteristics that continue to be in demand a decade after first commercial introductions are: (1) foliage color stability in sun and shade; (2) consistent well-branched plant habit; and (3) late flowering. Improved plants with interesting foliage colors in both full sun and shade conditions allow for more versatile garden use and more color choices for gardeners. Superior well-branched plant habit is important throughout the production chain from the propagator/grower to the consumer, which allows for production of a large number of vegetative propagules and translates into more manageable plants for producers during culture and shipping to retail outlets. Once planted in the garden, these well-branched plants require less management over a long season of growth. Late flowering is a desirable characteristic because early flowering triggers senescence of the lower leaves and decreases foliage quality of coleus. Floral induction often slows vegetative growth, and increases landscape maintenance with manual dead-heading and plant replacement, which is vital to landscape contractors. Late or 'no flowering' genotypes with good branching and stable foliage color that have been developed at UF have performed well in commercial markets, and continue to attract interest from U.S., European and Asian gardeners. The UF genotypes disclosed herein were selected because they have many of these desirable traits.

SUMMARY OF THE INVENTION

The invention relates to a new and distinct cultivar of coleus plant named 'UF17-64-1'. 'UF17-64-1' originated from an open pollination conducted in May-November 2016 in Gainesville, Fla. between the female coleus plant 'UF16-67-14' (unpatented) and an unknown male coleus plant. A single seedling was chosen in May 2017 for further asexual propagation in Gainesville, Fla. FIG. 1 shows the pedigree of 'UF17-64-1'.

'UF17-64-1' has been reproduced asexually for over 18 months through vegetative cuttings and has been found to retain its distinctive characteristics through successive asexual propagations. 'UF17-64-1' was first propagated asexually by meristem tip cuttings in May 2017 in Gainesville, Fla., and has remained true-to-type since that time.

The new coleus cultivar 'UF17-64-1' has not been observed under all possible environmental conditions. The phenotype of the new cultivar may vary with variations in environment and cultural practices such as temperature, light intensity, fertilization, irrigation, and application of plant growth regulators without any change in genotype.

'UF17-64-1' was selected based on several visual characteristics. The following traits have been repeatedly observed and are determined to be the unique characteristics of the new coleus cultivar. These characteristics in combination distinguish 'UF17-64-1' as a new and distinct cultivar of coleus:

1. vigorous growth with large leaves and a very consistent and well-branched plant habit when grown from vegetative propagules as a stock plant, thus providing ample vegetative propagules for producers;
2. excellent heat tolerance;
3. foliage color is a rich crimson color with no other markings, which is an extremely rare trait for red coleus plants; and
4. very consistent plant growth in both sun and shade conditions in Gainesville, Fla. and Citra, Fla.;
5. 'UF17-64-1' has not been observed to set flowers or seeds under trailing protocols, and has been observed to have long-season performance in landscape trials in Gainesville, Fla.

Plant of the new coleus cultivar 'UF17-64-1' differ from plants of the female parent, 'UF16-67-14', in the following characteristics:

1. 'UF17-64-1' has large leaves that are purely crimson in color with no markings, whereas the female parent 'UF16-67-14' has smaller leaves that are colored maroon and lime green; and
2. 'UF17-64-1' has a robust, well-branched mounded habit, whereas 'UF16-67-14' is slightly less vigorous and more upright in habit.

Plants of the new coleus cultivar 'UF17-64-1' are similar to those of commercial coleus cultivar 'UF0646' (U.S. Plant Pat. No. 21,585); however, 'UF17-64-1' has a spreading plant form, whereas 'UF0646' has a more upright plant form. Additionally, 'UF17-64-1' has an upper-surface leaf coloration of RHS 185A (Deep Red), whereas 'UF0646' has an upper-surface leaf coloration of RHS 46C (Red).

DESCRIPTION OF THE FIGURES

The accompanying photographs (as shown in FIGS. 2 and 3) illustrate the overall appearance of the new coleus cultivar 'UF17-64-1'. These photographs show the colors as true as can be reasonably obtained in colored reproductions of this type. Colors in the photographs may differ slightly from the color values cited in the detailed botanical description, which accurately describe the colors of the new coleus cultivar.

DETAILED BOTANICAL DESCRIPTION OF THE CULTIVAR

Figure 1:
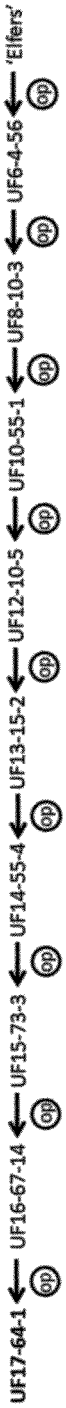
FIG. 1 shows the pedigree of 'UF17-64-1'.
Figure 2:
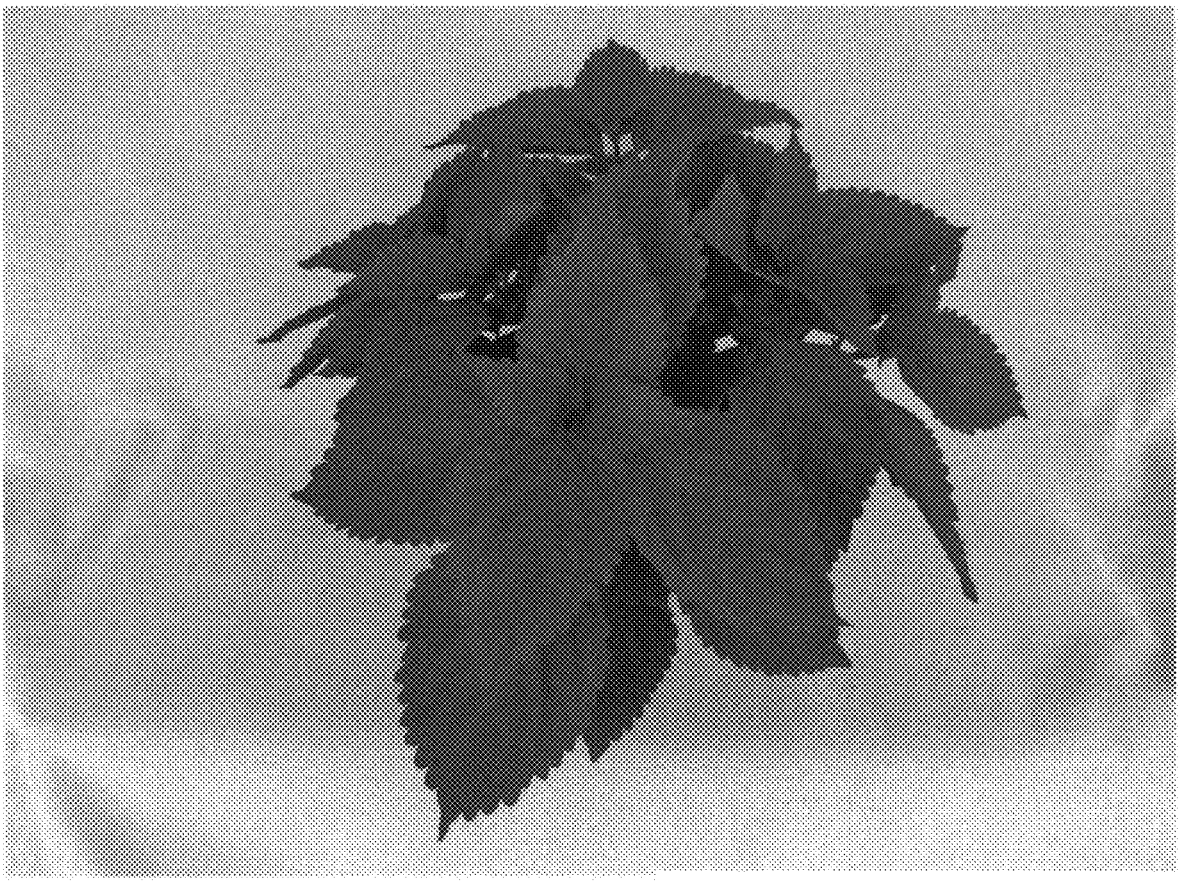
FIG. 2 shows the growth habit, form, and foliage of a nine-week-old plant of the new coleus cultivar 'UF17-64-1'.
Figure 3:
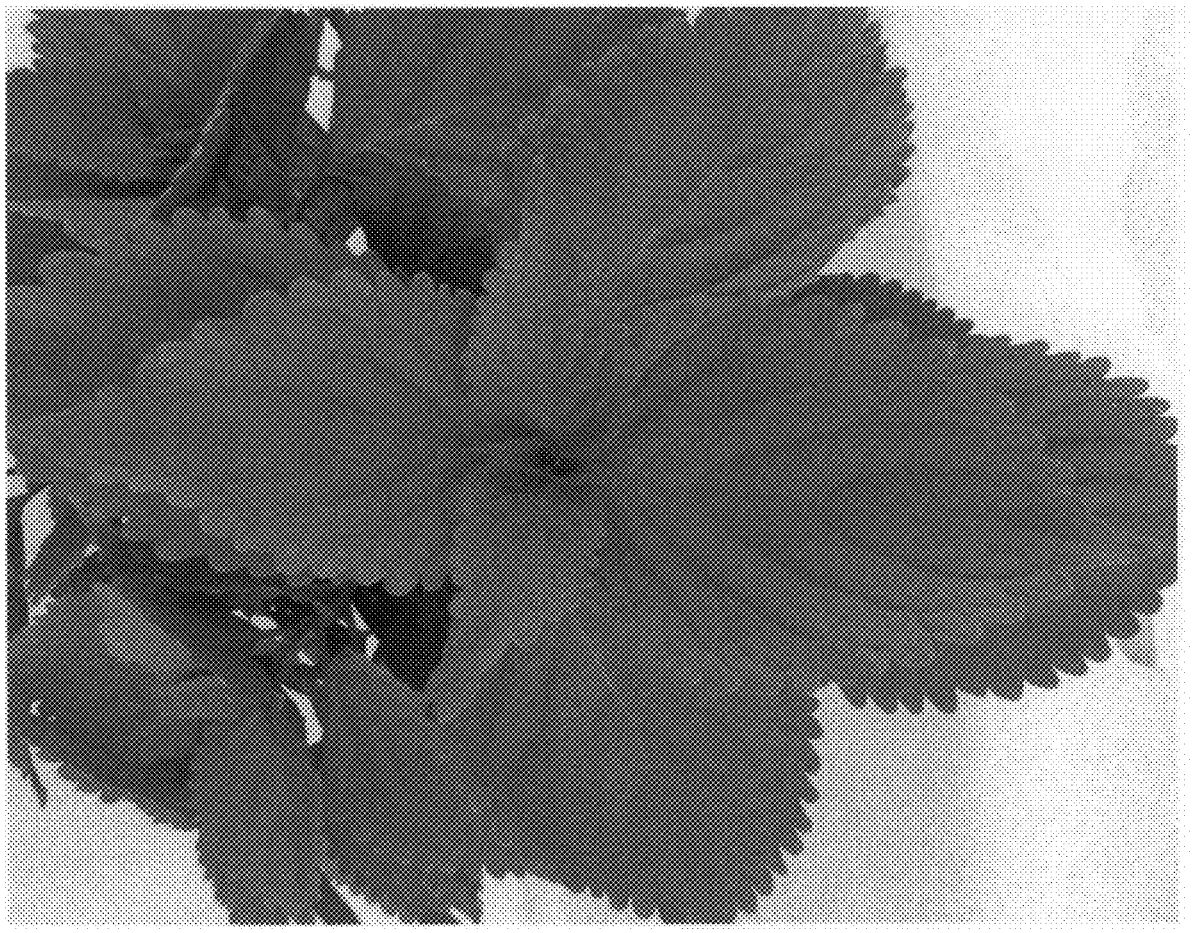
FIG. 3 shows a close-up view of the foliage of a nine-week-old plant of the new coleus cultivar 'UF17-64-1'.

The following detailed description sets forth the distinctive characteristics of the new coleus cultivar 'UF17-64-1' when grown under normal horticultural practices in Gainesville, Fla. and Citra, Fla. 'UF17-64-1' has the combination of vigorous, compact upright growth habit, excellent heat tolerance, and crimson colored leaves that are significantly different than other coleus plant. It has superior stability in foliage color in both sun and shade conditions, maintaining stable color in all conditions.

Botanical description:

*Botanical classification.*—Family: Lamiaceae. Botanical name: *Plectranthus scutellarioides*.Common name: Coleus. Cultivar: 'UF17-64-1'.

*Parentage.*—Female or seed parent: Coleus cultivar 'UF16-67-14'. Male or pollen parent: Unknown (open pollination was used).

*Propagation.*—Type: Cuttings; vegetative meristems having at least 1 node. Time to initiate roots: Approximately 3-4 days. Time to develop roots: Approximately 7-10 days.

*Root description.*—Root habit: Fibrous. Root description: Callus forms in approximately 2-3 days, roots initiate in approximately 3-4 days and become a highly branched cutting in approximately 7-10 days.

*Plant description.*—Plant form: Spreading. Growth habit: Upright. Plant height (from top of soil): Approximately 24-26 cm. Plant diameter (horizontal plant diameter): Approximately 50-55 cm. Branches: Quantity per plant: Approximately 7-8. Color: RHS N79B. Texture: Smooth. Pubescence: Not present. Stem description: Square-shaped stem, approximately 0.7 cm in diameter at the soil line. Branch diameter: Approximately 0.6-0.7 cm at the base of a 22-cm-long branch. Branch length: Approximately 21-23 cm. Internode length: Approximately 2-3 cm. Anthocyanin: RHS N79B.

*Foliage description.*—Quantity of leaves per branch: Approximately 17-19. Arrangement: Opposite. Fragrance: Not fragrant. Shape: Ovate. Length: Approximately 13-14 cm. Width: Approximately 9-10 cm. Apex: Broadly acuminate. Base: Attenuate. Margin: Crenate. Texture, upper and lower surfaces: Smooth. Pubescence color (both surfaces): Not present. Venation pattern: Upper surface: Arcuate. Lower surface: Reticulate. Color of veins: Upper surface: RHS 59B. Lower surface: RHS 187B. Color: Immature leaf: Upper surface: RHS 185A. Lower surface: RHS 187B. Mature leaf: Upper surface: RHS 185A. Lower surface: RHS 187B. Petiole: Length: Approximately 3-4 cm. Diameter: Approximately 0.2-0.3 cm. Color: RHS 187B. Texture: Smooth, no pubescence.

*Flowers and seeds.*—Flowers and seeds have not been observed to date during formal trials in Gainesville, Fla.

*Fruit.*—Fruit has not been observed to date during formal trials in Gainesville, Fla.

*Disease and insect resistance.*—Disease and insect resistance of the coleus cultivar 'UF17-64-1' is typical of the species, and therefore no claims are made herein of any superior disease or insect resistance The most commonly observed insect pests on this species in Gainesville, Fla. have been long-tailed or citrus mealybugs (*Pseudococcus* sp.), which occur on older stock plant material held in the greenhouse for over three to four months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the United States is downy mildew (*Peronospora lamii*), which has been observed in stock materials grown closely together in cooler growing seasons.

I claim:

1. A new and distinct *Plectranthus scutellarioides* (coleus) plant named 'UF17-64-1' as shown and described herein.

* * * * *